United States Patent [19]

Urquhart et al.

[11] Patent Number: 4,773,907

[45] Date of Patent: * Sep. 27, 1988

[54] PRIMARY DELIVERY SYSTEM COMPRISING SECONDARY DOSAGE FORM

[75] Inventors: John Urquhart, Palo Alto; Felix Theeuwes, Los Altos, both of Calif.

[73] Assignee: ALZA Corporation, Palo Alto, Calif.

[*] Notice: The portion of the term of this patent subsequent to Mar. 25, 2003 has been disclaimed.

[21] Appl. No.: 37,489

[22] Filed: Apr. 13, 1987

Related U.S. Application Data

[63] Continuation of Ser. No. 832,192, Feb. 24, 1986, Pat. No. 4,681,583, which is a continuation-in-part of Ser. No. 451,329, Dec. 20, 1982, Pat. No. 4,578,075.

[51] Int. Cl.⁴ ................................ A61J 3/00
[52] U.S. Cl. .................. 424/467; 424/452; 424/459; 424/473
[58] Field of Search .............. 604/890–897; 424/19–22

[56] References Cited

U.S. PATENT DOCUMENTS

| | | | |
|---|---|---|---|
| 3,786,813 | 1/1974 | Michaels | 604/892 |
| 3,917,813 | 11/1975 | Pedersen | 424/20 |
| 4,193,985 | 3/1980 | Bechgaard et al. | 424/19 |
| 4,263,273 | 4/1981 | Applegren et al. | 424/20 |
| 4,324,779 | 4/1982 | Dahlhausen et al. | 424/20 |
| 4,326,525 | 4/1982 | Swanson et al. | 604/892 |
| 4,339,428 | 7/1982 | Tencza | 424/21 |

FOREIGN PATENT DOCUMENTS 1204580  9/1970  United Kingdom ................. 424/37

Primary Examiner—C. Fred Rosenbaum
Assistant Examiner—Denise Whelton
Attorney, Agent, or Firm—Paul L. Sabatine; Edward L. Mandell; Steven F. Stone

[57] ABSTRACT

A delivery system is disclosed comprising a wall surrounding a lumen containing a plurality of dosage delivery devices. The wall is formed of an environment sensitive material that releases the dosage forms into the environment. The dosage forms comprise a semipermeable wall surrounding a compartment containing drug. A passageway through the semipermeable wall releases drug from the dosage form to the environment.

2 Claims, 1 Drawing Sheet

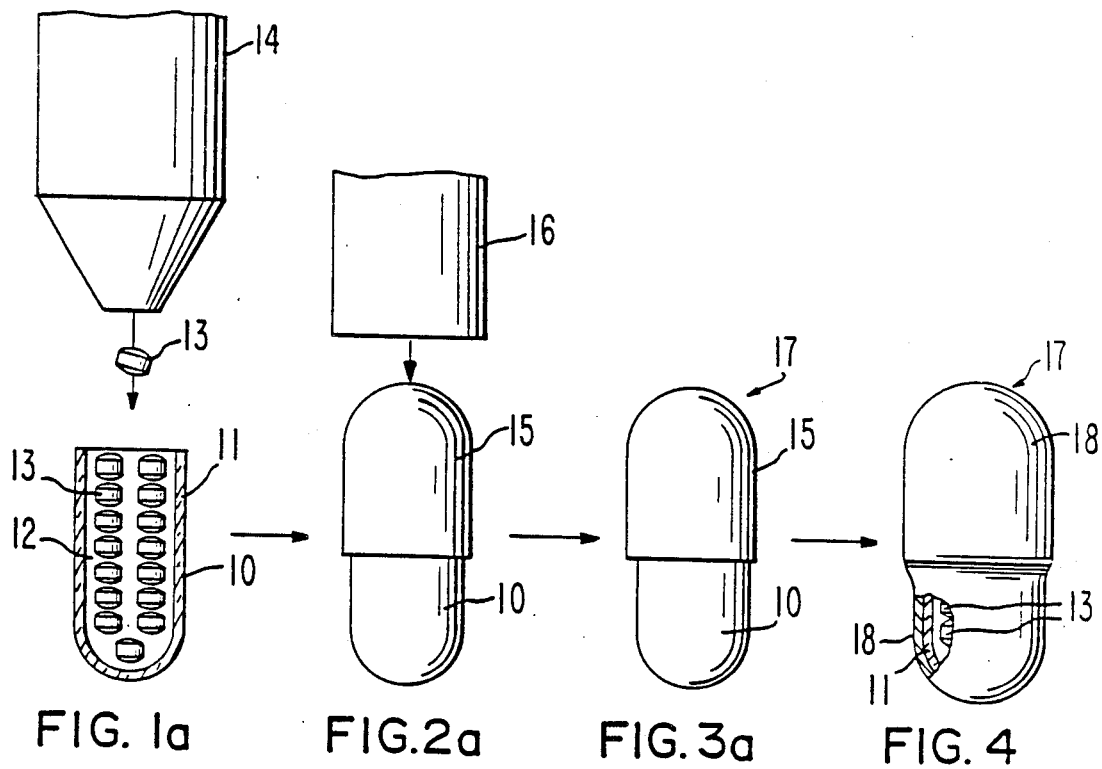
FIG. 1a  FIG. 2a  FIG. 3a  FIG. 4
FIG. 5
FIG. 6
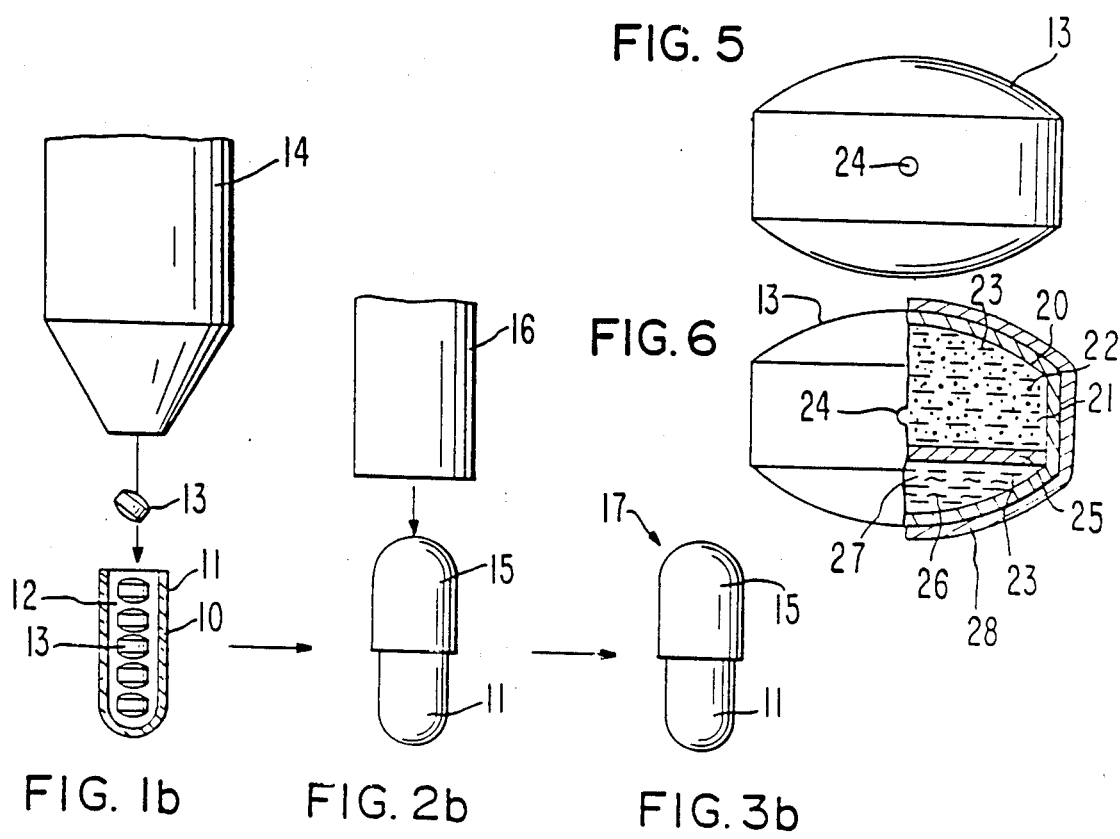
FIG. 1b  FIG. 2b  FIG. 3b

PRIMARY DELIVERY SYSTEM COMPRISING SECONDARY DOSAGE FORM

CROSS REFERENCE TO RELATED APPLICATIONS

This application is a continuation of Ser. No. 06/832,192 filed Feb. 24, 1986, now U.S. Pat. No. 4,681,583, issued July 21, 1987 which application is continuation-in-part of appln. Ser. No. 06/451,329 filed Dec. 20, 1982, now U.S. Pat. No. 4,578,075 issued Mar. 25, 1986.

FIELD OF THE INVENTION

This invention pertains to both a novel and unique delivery system. More particularly, the invention relates to a delivery system comprising an exterior wall that surrounds a lumen housing a plurality of dispensable dosage forms. The exterior wall is formed of an environment sensitive material that releases the dosage forms into the environment. The dosage forms comprise a wall that surrounds a compartment containing a drug with a passageway in the wall for delivering the drug overtime. The dosage form is useful for delivering a single drug, two drugs or more, that are separately housed and separately dispensed for (a) obtaining the therapeutic benefits of each drug, (b) lessening the incidence of adverse effects due to the incompatability of different drugs, (c) delivering at least two drugs that are difficult to deliver from a dispensing system, or (d) dispersing a drug in a preselected area of the gastrointestinal tract.

BACKGROUND OF THE INVENTION

Since the beginning of antiquity, both pharmacy and medicine have sought a dosage form for administering a beneficial drug. The first written reference to a dosage form is in the Eber Papyrus, written about 1552 B.C. The Eber Papyrus mentions dosage forms such as anal suppositories, vaginal pessaries, ointments, oral pill formulation, and other dosage preparations. About 2500 years passed without any advance in dosage form development, when the Arab physician Rhazes, 865-925 A.D., invented the coated bill. About a century later the Persian Avicenna, 980-1037 A.D., coated pills with gold or silver for increasing patient acceptability and for enhancing the effectiveness of the drug. Also around this time, the first tablet was described in Arabian manuscripts written by al-Zahrawi, 936-1009 A.D. The manuscripts described a tablet formed from the hollow impressions in two facing tablet molds. Pharmacy and medicine waited about 800 years for the next innovation in dosage forms, when in 1883 Mothes invented the capsule for administering drug. The next quantum leap in dosage forms came in 1972 with the invention of the osmotic dosage form by inventors Theeuwes and Higuchi. The osmotic dosage form is manufactured in one embodiment for oral use, and in this embodiment it embraces the appearance of a tablet with a drug delivery portal. It is the first oral dosage form that delivers a given amount of drug per unit time at a rate controlled by the dosage form over a prolonged period of time.

Also, since the beginning of antiquity, pharmacy and medicine sought a primary dosage form comprising a plurality of secondary dosage form that are released by the primary dosage form in a preselected region of the gastrointestinal tract, such as the stomach. A primary dosage form is needed for dispersing a plurality of secondary dosage forms in the stomach for their subsequent passage over time into the intestine and colon for administering a local or systemic therapy in the intestine and/or colon. A primary dosage form that immediately releases and diperses the secondary dosage form throughout the stomach, for their eventual passage from the stomach through the pylorus over a prolong period of time is achieved by physiologically maintaining the stomach in a feed mode. The secondary dosage unit cooperate over time the passage of the secondary dosage form for administration of drug in the intestine and/or colon.

It is desirable to prescribe pharmaceutical dosage forms containing at least two different drugs for obtaining the pharmacological benefits of each drug. The co-administration of certain drugs is prescribed often in fixed ratios for several reasons. For example, for drugs that have the same therapeutic effect but act mechanistically different on the body, such combinations may have the added therapeutic effect of both drugs but less side effects or the drugs may act synergistically and create a larger than additive effect. Drug combinations are prescribed for treatments where each individual drug address different symptoms of a particular medical situation. Although, a large number of therapeutic combinations could be provided, often they can not be compounded in the same dosage form because each drug needs to be administered on a different schedule. The different schedule is needed because each drug has a different biological half life and therapeutic index and therefore each drug should be administered in separate dosage forms on a prescribed schedule that is specific for each drug. Thus, a drug that needs to be administered four times a day, should not be combined with a drug that should be administered once a day. These drugs are kinetically incompatible in a pharmaceutical dosage form. Another reason why certain drugs cannot be combined is they may be chemically incompatible or unstable in the presence of each other. This kinetic or chemical incompatibility can be eliminated by the novel dosage form provided by this invention. For example, by using the dosage form provided by this invention, a regimen consisting of four times a day administration of drug can be transformed into a once a day administration such that the drug previously administered four times daily can be combined with a drug adiministered once daily. In other words, both drugs can be co-administered to the body at delivery rates that are matched to achieve each of their separate therapeutic plasma concentrations.

In the light of the above presentation, it will be appreciated by those versed in the dispensing art, that an improved delivery system comprising a primary delivery member that dispenses a plurality of secondary delivery members in the stomach followed by their timed-passage into the intestine and colon for administering a drug therein, such a delivery system would have definite use and be a valuable contribution to the dispensing arts. It will also be appreciate that a novel delivery system housing a drug, or two, or more different drugs for independent or for simultaneous independent co-delivery, at continuous and controlled rates in therapeutically effective amounts for obtaining the benefits of each drug, such a delivery system would have a definite use and be a valuable contribution to the dispensing arts. The present invention additionally advances the state of the dispensing art by making available a primary delivery system housing a number of independent delivery portal pre-manufactured or formed during use for increasing the bioavailability of the drug, the administration of the drug in a drug receiving environment and concomitantly decreasing the likelihood of local unwanted effects, and for dispensing at least one drug, or at least two different drugs to a biological receptor substantially free of interaction and drug incompatibility.

OBJECTS OF THE INVENTION

Accordingly, in view of the above presentation it is an immediate object of this invention to provide both a novel and useful drug delivery system that makes a substantial contribution to the art by providing a delivery system useful for obtaining better therapy in the management of health and disease.

Another object of the invention is to provide a delivery system that further perfects drug delivery by having the combined effects of dispersing delivered drug in the biological environment for improving its availability, its absorption and for minimizing local irritation of the biological drug receiving environment.

Another object of the invention is to provide a delivery system for administering a drug in the gastrointestinal tract with a system that is relatively economical in cost to manufacture, provides the clinician with a dependable delivery system, and is well-adapted for practical and acceptable patient use.

Another object of the invention is to provide a primary delivery system for releasing a plurality of secondary dosage forms in the gastrointestinal tract which dosage forms are manufactured as miniature osmotic drug delivery devices that diffuse and spread a delivered drug over a larger area of the gastrointestinal tract such as the intestine or colon.

Another object of this invention is to provide a delivery system comprising a multiplicity of tiny oral, osmotic drug delivery devices that are simple in construction and exhibit all the practical benefits of controlled an continuous administration of drug during their residency in the stomach and/or the intestine for executing a therapeutical program.

Another object of the invention is to provide a delivery system comprising (1) a plurality of tiny osmotic delivery devices, and (2) a wall surrounding a lumen housing the plurality of osmotic devices, the wall formed of (a) a material that releases the tiny devices into an environment having pH of 1.0 to 3.5 inclusive, or (b) a material that maintains its physical and chemical integrity in an environment having a pH of 1.0 to 3.5 inclusive, and releases the tiny devices in an environment having a pH of greater than 3.5 to 8.0.

Another object of this invention to provide a delivery system that contributes to the dispensing art by making available a system that can dispense at least two different drugs at controlled rates for obtaining the pharmacological and physiological benefit of each drug, and which system thusly represents an improvement and an advancement in the delivery arts.

Another object of the invention is to provide a delivery system housing osmotic dosage form devices for separately housing and separately dispensing two drugs essentially-free of chemical interactions attributed to chemical incompatibility, thereby overcoming the problems associated with the prior art. Another object of the invention is to provide a delivery system comprising osmotic dosage form devices embracing different structures and different sizes for dispensing a drug to selected loci of the gastrointestinal tract over time.

Another object of the invention is to provide both a novel and useful primary delivery system as a means for providing a plurality of tiny dosage forms for dispersion in the stomach that are kept in the stomach by maintaining the stomach in the fed mode for extended residency for making them available therein for their subsequent passage into the intestine.

Another object of the invention is to provide a means for executing a therapeutic program, which means comprises a primary delivery system that releases a plurality of dosage forms in the stomach that are kept in the stomach by keeping the stomach in a fed mode thereby enabling the release of the dosage forms from the stomach over time.

Another object of the invention is to provide a plurality of enteric-coated tiny osmotic dosage forms for delivering a drug in the intestine.

These objects, as well as other objects, features and advantages of the invention, will become more apparent from the following detailed description of the invention, the drawings and the accompanying claims.

BRIEF DESCRIPTION OF THE DRAWINGS

In the drawings, which are not drawn to scale, but are set forth to illustrate various embodiments of the invention, the Figures are as follows:

FIGS. 1a and 1b are views partly in section of an opened wall primary member with an internal space receiving a plurality of miniature secondary dosage forms, manufactured in the shape of delivery device, from a filling hopper;

FIGS. 2a and 2b are partial, diagrammatic views of filled wall member of FIGS. 1a and 1b being capped for closing the wall member;

FIGS. 3a and 3b illustrate drug delivery dosage systems provided by the invention;

FIG. 4 illustrates the delivery dosage system of FIG. 3a comprising an additional outer wall for regulating the release of drug delivery device from the delivery system;

FIG. 5 depicts an oral osmotic drug delivery device housed in the delivery system; and, FIG. 6 is an opened view of the delivery dosage device of FIG. 5 for illustrating the structure of the delivery device.

In the drawings and the specification, like parts in related Figures are identified by like numbers. The terms appearing earlier in the specification, and in the description of the drawings as well as embodiments thereof, are further described elsewhere in the disclosure.

DETAILED DESCRIPTION OF THE DRAWINGS

Turning now to the drawings in detail, which drawings are an example of the delivery system and the manufacturing procedure provided by the invention, and which examples are not to be construed as limiting, one example of the delivery system and the manufacturing procedure is seen in FIGS. 1 through 6, considered together.

FIGS. 1a and 1b illustrate one manufacturing step in the assembly leading to a delivery dosage system provided by the invention. FIGS. 1a and 1b depict in opened section a body portion 10 comprising a wall 11 surrounding an internal lumen 12. Wall 11 is formed of (a) a material that immediately releases the contents of the delivery system, when the system enters an environment having a pH of 1.0 to 3.5 inclusive, or (b) a material that maintains its physical and chemical integrity in an environment having pH of 1.0 to 3.5 inclusive, but releases the contents of the delivery system when it enters an environment having a pH of greater than 3.5 to 8.0. Wall 11 surrounds and forms internal lumen 12 and in the embodiment illustrated in FIGS. 1a and 1b it is made as the receiving portion shaped like a capsule. Internal lumen 12 is receiving a multiplicity of tiny dosage forms 13, from hopper 14. Hopper 14 feeds a predetermined number of tiny dosage forms 13 into lumen 12. Wall 11 that surrounds and forms internal lumen 12 is a primary delivery system housing a plurality of secondary dosage forms 13. The secondary dosage forms 13, in a preferred embodiments are osmotic dosage forms for administering a drug in the gastrointestinal environment of use.

FIGS. 2a and 2b illustrate another step in the manufacture of the delivery system 10. In FIGS. 2a and 2b body portion 10 is telescopically capped with an engaging cap portion by a capping hopper 16 to yield the primary dosage system 17 as seen in FIGS. 3a and 3b.

FIG. 4 illustrates primary delivery system 17 of FIG. 3a comprising an additional outer wall 18. Outer wall 18 is formed of a delayed release material that keeps its integrity in an environment having a pH of 1.0 to 3.5 inclusive, but releases secondary delivery devices 13 housed therein when the primary delivery system 17 passes into an environment having a pH greater than 3.5 to 8.0. Outer wall 18 is an embodiment that can be used when inner wall 11 is made from a material that would release the delivery devices in an environment having a pH of 1.0 to 3.5 inclusive, and it is desired to delay their release until the delivery system enters an environment having a pH of 3.5 to 8.0.

FIGS. 5 and 6 illustrate secondary dosage forms 13 manufactured as an osmotic delivery device 13 sized and shaped for housing in primary delivery system 17. Delivery device 13 of FIG. 5 is seen in opened section in FIG. 6. Delivery device 13 comprises a wall 20 comprising in at least a part, or totally, a semipermeable composition that surrounds and defines an internal compartment 21. Semipermeable wall 20 is permeable to the passage of an external fluid present in the environment of use and it is substantially impermeable to the passage of drug and osmotically effective compounds known as osmagents. Compartment 21 contains a drug 22 that is soluble in fluid imbibed into compartment 21 and it exhibits an osmotic pressure gradient across semipermeable wall 20 against an external fluid. In another embodiment, compartment 21 contains a drug 22 that has limited solubility in fluid that enters compartment 21 and is mixed with an osmotically effective compound that is soluble in fluid 23 imbibed into compartment 21 and exhibits and osmotic pressure gradient across wall 20 against an external fluid.

An exit means 24 is present in wall 20 that communicates compartment 21 with the exterior of device 13 for delivering drug 22 or a controlled and continuous rate over a prolonged period of time. The expression exit means 24 embraces at least one passageway or orifice that passes through wall 20. The exit means includes also bore, pore, porous element through which a drug can migrate, a hollow fiber, capillary tube, and the like. The expression also includes a material that erodes or is leached from wall 20 in a fluid environment of use to produce at least one passageway in the secondary dosage form 13. Representative materials suitable for forming at least one passageway, or a multiplicity of passageways include an erodible poly(glycol) or poly(lactic) acid member in the wall, a gelatinous filament, poly(vinylalcohol), leachable materials such as fluid removable pore forming salts, oxide, polysaccharides and the like. A passageway can be formed by leaching a material such as sorbitol from the wall. The passageway can be formed by wall 20 bursting to form a passageway of controlled dimensions in operation of secondary dosage form 13. The passageways can have any shape, such as round, elliptical and the like. The device can be constructed with one or more passageways in a spaced apart relation on more than a single surface of the dosage form. Passageways and equipment for forming passageways are disclosed in U.S. Pat. Nos. 3,845,770; 3,916,899; 4,063,064 and 4,088,864. Passageways formed by leaching are disclosed in U.S. Pat. No. 4,200,098. Passageways formed by osmotic bursting pressure are disclosed in U.S. Pat. No. 4,016,880.

Dosage 13 can be formed in an embodiment, optionally with an internal partition 25. Partition 25 comprises an expandable material to define an expansion compartment 27. Compartment 27 contains an expandable member 26 that is (a) an osmagents or (b) an osmopolymer. In either embodiments, the osmagents, or the osmopolymer imbibes and absorbs fluid from the environment of use causing compartment 27 to (c) fill with solution containing osmagent, or to (d) fill with an expanding osmopolymer, thereby urging in (c) or (d) partition 25 to expand and assist compartment 21 in dispensing drug 22 through passageway 24 from device 13. In a preferred embodiment, when compartment 27 comprises an osmopolymer, dosage form 13 is manufactured without partition 25. In this manufacture, osmopolymer 26 expands into compartment 21 directly against drug layer 22 thereby pushing drug 22 through passageway 24 of dosage form 13.

DETAILED DESCRIPTION OF THE INVENTION

In accordance with the practice of this invention, delivery system 17 comprising a wall 11 that surrounds an internal lumen 12 can in one embodiment be made as a capsule. The capsules are made of tasteless materials, they are easily filled and they are easily self-administered by a patient in readily assimilable form. The capsules are conveniently made in two parts, with one part slipping over the other part for completely surrounding delivery device 13 housed therein. The capsules can have a variety of sizes from triple zero to five. The capsules used for the purpose of the invention can be transparent and colorless, or colored capsules can be used to give a special product a distinctive appearance. The capsules can be filled with the drug delivery devices by manual or machine filling methods.

The materials useful for forming wall 11 of delivery system 17 that instantly release delivery device 13 in an environment having a pH of 1.0 to 3.5 inclusive are materials that have a glass transition temperature greater than room temperature, and change their integrity in this environment and concurrently release the delivery devices. The presently preferred materials are pH-sensitive, nontoxic, physiologically inactive, and do not adversely effect the drug and a host. The materials dissolve, disintegrate, degrade, hydrolyze, solubilize, are digested, or undergo like change in this biological pH environment. The product produced, as the material changes and releases the tiny osmotic delivery device, is nontoxic, chemically inert, and physiologically inactive. One group of presently preferred materials are polymers, such as proteins having a peptide bond like gelatin of the soft or hard type.

The materials used for forming wall 11 of delivery system 17 that maintains its physical and chemical integrity in an environment having a pH of 1.0 to 3.5 inclusive, and instantly releases delivery device 13 in an environment having a pH of greater than 3.5 to 8.0 are materials such as (a) polymers having at least one acidic group that enables it to keep its integrity in the lower pH environment, but releases the reservoirs in the higher pH environment, (b) polymers that undergo changes in the higher pH environment by enzymes present in that environment, (c) polymer compositions comprising a polymer and another agent that promote compositions comprising a polymer and another agent that promote at the higher pH the disintegration of the wall, and the like. Exemplary material that can be used that keep their integrity at a pH of 1.0 to 3.5 inclusive are cellulose carboxylic acid esters phthalates, carboxylic acid ethers phthalates, such as cellulose ethyl phthalate, cellulose acetate phthalate, starch acetate phthalate, amylose acetate phthalate, hydroxypropyl methylcellulose phthalate, hydroxypropyl methylcellulose hexahydrophthalate, and the like. Polyacidic acids that keep their integrity at a pH of 1.0 to 3.5 inclusive, having acid groups in an associated form in the pH range, such as vinyl derivatives of partially hydrolyzed styrene-maleic anhydride copolymer, methylmethacrylate-methacrylic acid copolymer, polymethacrylic acid ester, methylacrylate-methacrylic acid ester, partial alkylene glycol ether esters of $C_1$ to $C_4$ alkyl acrylate unsaturated carboxylic acid anhydride co-polymers including maleic, citraconic or itaconic carboxylic acid anhydride, and the like.

Representative of other polymers, and other polymer compositions that comprise at least two ingredients operable for the present purpose of keeping their integrity in a pH range of 1.0 to 3.5 inclusive, are polymers such as shellac, ammoniated shellac, formalized gelatin, polyvinyl acetate phthalate, polyvinyl acetate hydrogenphthalate, and the like; polymer compositions such as a mixture of hydroxyphenyl methylcellulose phthalate and triacetate glycerol in a weight-to-weight ratio of 99-to-1, shellac-formalized gelatin composition, styrene-maleic acid and polyvinyl acetate phthalate composition, shellac and stearic acid composition, and the like.

Semipermeable materials operable for forming wall 20 of delivery device 13 are materials insoluble in body fluids, and they are nonerodible. Typical materials for forming wall 20 include semipermeable polymers such as cellulose acylate, cellulose diacylate, cellulose triacylate, cellulose acetate, cellulose diacetate, cellulose triacetate, and the like. Other semipermeable polymers include polyurethane and selectively permeable polymers including polyurethane, selectively permeable polymers formed by the coprecipitation of a polycation and a polyanion. Generally, semipermeable polymers useful for forming wall 20 will have a fluid permeability of $10^{-5}$ to $10^{-1}$ (cc mil/cm$^2$ hr atm) expressed as per atmosphere of hydrostatic or osmotic pressure difference across wall 20 at the temperature of use. Procedures leading to the manufacture of osmotic devices are described in U.S. Pat. No. 3,845,770 and 3,916,899.

Procedures leading to the manufacture of an osmotic device embracing a drug and an expansion compartment separated by a partition are disclosed in U.S. Pat. No. 4,111,202.

Dosage form B in another embodiment carries a pH sensitive layer 28 on the exterior surface of wall 20. The pH sensitive material keep its integrity, that is it does not dissolve or erode, in a pH of 1.0 to 3.5, and it looses its integrity in a pH of 3.5 to 8.0. Representative materials for forming layer 28 are the pH sensitive materials set forth above. In a presently preferred embodiment the pH sensitive materials are cellulosic phthalates such as a member selected from the group consisting of a cellulosic phthalate, cellulose acyl phthalate, cellulose alkyl phthalate, cellulose ethyl phthalate, cellulose acetate phthalate, starch acetate phthalate, amylose acetate phthalate, hydroxypropylcellulose phthalate, hydroxypropylmethylcellulose phthalate, alkali salts of cellulose acetate phthalate such as the sodium salt of cellulose acetate phthalate, alkaline earth salts of cellulose esters such as the calcium salt of cellulose acetate phthalate, ammonium salts of acidic cellulose esters such as ammonium salt of hydroxypropyl methylcellulose phthalate, cellulose acetate hexahydrophthalate, hydroxypropyl methylcellulose hexahydrophthalate, and the like.

The osmotically effective solutes useful in compartment 21 include inorganic and organic compounds that exhibit an osmotic pressure gradient across semipermeable wall 20 against an external fluid. Osmotically effective solutes useful for the present purpose include magnesium sulfate, lactose, urea, inositol, raffinose, sucrose, glucose, lactose, sorbitol and mixtures thereof. Osmotically effective agents and their osmotic pressure in atmospheres are disclosed in U.S. Pat. No. 4,210,139.

The osmotically effective osmopolymers useful for urging the drug from the compartment includes polymeric members that are hydrophilic, interact with fluids and swell to an equilibrium state, and retain a significant portion of the imbibed or absorbed fluid within the hydrophilic structure. The hydrophilic polymers from their nonhydrated state swell or expand to a very high degree, usually exhibiting a greater than 2 fold volume increase, usually a 2 to 50 fold volume increase in fluid. Representative hydrophilic polymers include poly (hydroxyalkyl methacrylate); poly(vinyl pyrrolidone) having a molecular weight of 10,000 to 360,000; poly(ethylene oxide) having a molecular weight from 10,000 to 5,000,000; carboxyvinyl polymer; sodium acidic carboxyvinyl hydrogel; potassium acidic carboxyvinyl hydrogel; and the like.

In the specification and the accompanying claims, the term drug includes any substance that produces a local or systemic effect, or effects in animals, avians, reptiles and pisces. The term animal includes warm-blooded mammals, primates, humans, household, sport, farm, laboratory and zoo animals. The phrase drug formulation as used herein means drug 22 is in compartment 21 by itself, or drug 22 is in compartment 21 mixed with an osmotic solute, binder or the like. The active drug that can be delivered includes inorganic and organic drugs that act on peripheral nerves, adrenergic receptors, cholinergic receptors, nervous system, skeletal muscles, cardiovascular system, smooth muscles, blood circulatory system, synoptic sites, neuroeffector junctional sites, endocrine and hormone systems, immunological system, reproductive system, skeletal system, autacoid system, tissues, organs, alimentary and excretory systems, inhibitory systems, histamine systems, body passageways, and the like. The drug includes for example, hypnotics, sedatives, psychic energizers, tranquilizers, anti-convulsants, muscle relaxants, antiparkinson, antipyretics, anti-inflammatory, analgesics, steroids, anticholinergics, antispasmodics, polypeptides, anesthetics, hormones, anti-microbials, sympathomimetics, cholinergies, diuretics, neoplastics, hypoglycemics, amino acids, opthalmics, vitamins, and the like. The delivery system in one embodimet can house osmotic delivery device containing the same drug, and in another embodiment the delivery system can house osmotic delivery devices containing like and unlike drugs. The inventive advantage provided by the osmotic devices each containing different drugs is that interaction among drugs that adversely effect each other is avoided, leading to better stability of delivered drug, and drug is delivered in the gastrointestinal tract substantially free of irritating the gastrointestinal mucus tissues. Also, drugs that have different rates of hydrolysis, different rates of oxidation, different rates of decomposition, different rates of delivery and different rates of bio-need can now be made into dosage form and dispensed essentially free of one drug influence or effecting another drug. The delivery system can house in the internal space both delivery devices and drug, which latter drug is available for instant use by a host, or the semi-permeable wall of the osmotic device can carry an enteric coating for delayed release of drug. The present invention provides a delivery system for administering drug, by making available a delivery system comprising osmotic devices representing a plurality of preformed passageways for dispensing and dispersing drug, and for enhancing its availability for use in better therapy. In a presently preferred embodiment the drugs include alpha adrenoceptor agonists with mixed $alpha_1/alpha_2$ selectively including clonidine, guanfacine, guanabenz, tiamenidine, lofexidine, alphamethylnorepinephrine, azepexole, naphazoline, tramazoline, tetryzoline, osymetazoline, and xylometazoline, $alpha_2$ agonist lidamidine, calcium channel blockers including loperamide, verapamil, diltiazers, nifedipine and congeners, fostedil, anticholinergics including atropine, homatropine, scopolamine, butylscopolamine, methylatropine, spasmolytics including papaverine and congeners, naloxone, $PGE_2$, and the like. The beneficial drugs, are known to the dispensing and in *Pharmaceutical Sciences,* by Remington, 14th Ed., 1970, published by Mack Publishing Co., Easton, Pa.; and *The Pharmacological Basis of Therapeutics,* by Goodman and Gilman, 4th Ed., 1970 published by MacMillan Co., London.

Drug 22 can be present in compartment 21 in various forms, such as uncharged molecules, molecular complexes, as therapeutically acceptable addition salts, such as hydrochlorides, hydrobromides, sulfates, oleates and the like. For acid drugs, salts of metals, amines, organic cations, quaternary ammonium salts can be used. Derivatives of drugs such as esters, ethers and amides can be used. A drug that is water insoluble can be used in a form that is water soluble derivative thereof to serve as a solute, and on its release from the delivery system is converted by enzymes, hydrolyzed by body pH, or other metabolic processes to the original biologically active form. The amount of drug in compartment 21 of a tiny dosage delivery device 13 generally is about 10 ng to 50 ng. The number of devices in a delivery system is at least two or more, more preferably about 5 to 750, and still more preferably about 5 to 100. The dosage forms can be the same size or of different size combinations, usually from 0.5 mm to 10 mm, with a preferred size of 3 to 10 mm diameter.

The drug delivery device 13 used for the purpose of the invention, is manufactured by standard techniques. For example, in one embodiment drug and a binder are mixed into a solid, semi-solid, or pressed into a miniature shape formed by conventional methods. Then, wall forming material is applied by molding, spraying or dipping the pressed drug shape into the wall forming material. In another embodiment, a wall can be cast, shaped to the desired dimensions that surround compartment 21, the compartment filled with drug, closed, and a passageway drilled through the wall. For osmotic devices manufactured smaller than 2 mm in diameter, the passageway is preferably made by the in situ method described in U.S. Pat. No. 4,016,880. In a presently preferred embodiment the delivery device is made by using an air suspension technique. This process consists in compressing a drug, and then suspending and tumbling the drug in a wall forming composition until the wall is applied around the drug. Next, after drying, a passageway is drilled in the wall. The air suspension procedure is described in U.S. Pat. No. 2,799,241; in *J. Am. Pharm. Assoc.,* Vol. 48, pages 451 to 459, 1959; and ibid., Vol. 49, pages 82 to 84, 1960. Other wall forming techniques such as pan coating can be used in which materials are deposited by successive spraying of the polymer solution on the drug, or solute, accompanied by tumbling in a rotating pan. Generally, a semipermeable wall will be about 0.01 to 10 mils thick, usually 1 to 3 mils. Of course, thinner and thicker walls are within the scope of the invention.

Delivery system 17 comprising body member 10 can be made by procedures such as dipping a mold element, having a shape corresponding to the shape illustrated in FIG. 1a or 1b for example, into a bath of a wall 11 forming material, such as a solution of aqueous gelatin. The mold element is submerged within the aqueous gelatin to form the desired coat on the mold element. Next, the coated mold is pulled from the solution, allowed to cool, and then stripped from the mold to yield the wall member with an internal lumen. The wall can be made from enteric material by dissolving, for example, dydroxypropyl methylcellulose phthalate in an aqueous solution of an alkali base to obtain an aqueous solution corresponding to the alkali metal salt of hydroxypropyl methylcellulose phthalate. Typical alkali bases are sodium carbonate, potassium carbonate, sodium hydroxide, and the like. Next, an aqueous gelatin solution is added to the solution of the alkali metal salt of hydroxypropyl methylcellulose phthalate, and molds immersed into the solution, withdrawn and the materials on the molds cooled at room temperature, or lower. Next, the capsule portion is removed from the mold. Manufacturing procedures for making capsules are disclosed in U.S. Pat. Nos. 1,527,659; 2,299,039; and 3,826,666.

Exemplary solvents suitable for manufacturing semipermeable wall 20 are inert inorganic and organic solvents that do not adversely harm the wall forming materials, the drug and the final osmotic device. The solvents broadly include aqueous solvents, alcohols, ketones, esters, ethers, aliphatic hydrocarbons, halogenated solvents, cycloaliphatic aromatics, heterocyclic solvents and the like. Typical solvents include acetone, methanol, ethanol, isopropyl alcohol, methyl acetate, ethyl acetate, methyl isobutyl ketone, n-hexane, methylene chloride, ethylene dichloride, mixtures such as acetone and water acetone and methanol, acetone and ethyl alcohol, methylene dichloride and methanol, ethylene dichloride and methanol, and mixtures thereof.

DESCRIPTION OF EXAMPLES

The following examples will serve to further illustrate the present invention, and they should not be considered as limiting the scope of the invention in any way, as these examples and other equivalents thereof will become apparent to those versed in the art in the light of the present disclosure, drawings, and the accompanying claims.

EXAMPLE 1

First, 100 mg of procainamide hydrochloride and 5 mg of binder polyvinyl pyrrolidone are blended into a homogeneous composition and passed through a 20 mesh screen to form a number of pre-cores of drug. The pre-cores next are compressed into round cores about 5 mm in diameter and then transferred to an air suspension machine. The compressed drug cores contain about 20 mg of drug and are coated with cellulose acetate having an acetyl content of 32% using a 5% polymer solution in dioxane to produce tiny osmotic drug delivery devices having a semi-permeable wall about 6 mils thick. After the delivery devices are dried for 10 days at about 55° C., an osmotic passageway about 4 mils in diameter is laser drilled through the semipermeable wall. Finally, a number of receiving capsules are filled with 5 osmotic devices and capped with the closing portion of the capsule to yield the delivery system. The wall of the delivery system comprises polymeric gelatin that releases the delivery devices in an environment having a pH of 1.0 to 3.5 inclusive.

EXAMPLE 2

A delivery device is made by first preparing drug reservoirs comprising potassium chloride by blending 1 kg of potassium chloride and 3 ml of a 20% solution of acacia to form a homogeneous blend. Next, the blend is passed through an extrusion granulation machine, dried at 115°–120° F. for 12 hours, and the reservoir forming cores passed through a 20 mesh screen. The cores are coated next in an air suspension machine with a 5% solution of cellulose acetate in a methylene chloride-methanol solvent, 89:11 wt:wt, with a semipermeable wall 7 mils thick. The coated drug is dried at 55° C. for 48 hours in an air oven, and then osmotic passageways are laser drilled in each device. The passageway had a diameter of about $42 \times 10^{-1}$ mils.

The tiny osmotic delivery devices are transferred to a feeding hopper and 15 devices are fed into the receiving portion of a capsule, and then the filled portion is moved to the next position in the filling line where the receiving portion is telescopically capped with an engaging cap portion to produce the completed delivery system. The receiving and cap portions are made from a wall forming composition comprising cellulose acetate phthalate and formalized gelatin, which composition keeps its integrity at a pH of 1.0 to 3.5 inclusive, and releases the tiny osmotic devices at a pH of greater than 3.5 to 8.0.

EXAMPLE 3

Drug delivery devices are prepared according to the procedures of the above examples. The drug reservoirs for this example are made from 375 g of aminophylline, 15.5 g of mannitol, and 1.5 g of magnesium stearate, and formulated into tiny compressed drug cores. The cores are coated with a semipermeable wall of cellulose acetate having an acetyl content of 38.3%, and a passageway laser drilled therethrough. Then, 15 of the tiny drug delivery devices are surrounded by a wall having first or inner lamina of gelatin, and then a second, or outer lamina of hydroxypropyl methylcellulose phthalate is laminated onto the inner lamina by dipping the delivery system with a bath containing hydroxypropyl methylcellulose phthalate.

EXAMPLE 4

The drug delivery systems prepared according to Example 1 are placed in an air suspension machine, and a volatile coating composition comprising an acrylic based resin in isopropyl alcohol is injected through a port into the machine for applying a coat onto the delivery system.

EXAMPLE 5

An osmotic delivery device for the controlled and continuous delivery of the beneficial drug hydralazine hydrochloride to a biological environment of use is made as follows: first a compartment forming composition is compounded from 50 mg of hydralazine hydrochloride, 208.5 mg of mannitol, 8 mg of hydroxypropyl methylcellulose and 8 mg of stearic acid by mixing the hydralazine hydrochloride and the mannitol and then passing the mixture through a 40-mesh screen; next, the hydroxypropyl methylcellulose is dissolved in 70/30 w/w % ethanol-water solution and the hydralazine mannitol mixture added to the wet hydroxypropyl methylcellulose and all the ingredients blended for 10 minutes. Next, the blend is passed through a 10-mesh screen and spread on a tray and dried in a forced air oven at 50° C. for 18–24 hours. The dried blend is passed through a 20-mesh screen, placed in a mixer, and the stearic acid added to the blend and the mixing continued for 10 minutes. Then, 35 mm of the hydralazine drug formulation reservoir is pressed under a pressure head into a 4 mm core and then coated in an air suspension machine with a wall of semipermeable cellulose acetate composition comprising 40% cellulose acetate having an acetyl content of 32%, 42% cellulose acetate having an acetyl content of 39.8%, and 18% hydroxypropyl methylcellulose, coated from an 80 to 20 parts by weight solvent of methylene chloride-methanol solvent. The coated osmotic device is dried in a forced air oven at 50° C. for one week, and then a laser passageway is drilled through the semipermeable wall.

A different reservoir forming composition comprising 19 mg of metoprolol fumarate, 1.4 mg of sodium bicarbonate, 1.6 mg of polyvinyl pyrrolidone and 0.32 mg of magnesium stearate is made by first mixing the metoprolol fumarate with sodium bicarbonate and passing the mixture through a 40-mesh screen, then, the polyvinyl pyrrolidone is mixed with 2 ml of an ethanol and 1 ml of water solution, and the freshly prepared polyvinyl pyrrolidone solution is added slowly with mixing to the metoprolol fumarate sodium bicarbonate mixture. The ingredients are mixed for 20 minutes, passed through a 10-mesh screen and dried in a forced air oven for 24 hours. Next, the dried blend is passed through a 20-mesh screen, placed in a mixer, the magnesium stearate added and the ingredients again blended to yield the reservoir ccmposition. Then, the metoprolol fumarate drug formulation is compressed into a solid core and coated in an air suspension machine with a wall of semipermeable cellulose acetate composition comprising 40% cellulose acetate having an acetyl content of 32%, 42% cellulose acetate having an acetyl content of 39.8%, and 18% hydroxypropyl methylcellulose, from an 80 to 20 parts by weight solvent of methylene chloride-methanol solvent. The coated osmotic device is dried in a forced air oven at 50° C. for one week, and then a laser passageway is drilled through the semipermeable wall. Finally a plurality of the osmotic devices containing the hydralazine and a plurality of the osmotic devices containing the metoprolol are charged into the lumen of a housing to yield the delivery system. The osmotic devices on their release from the housing in a gastrointestinal tract deliver the drugs with dispersion throughout the tract substantially free of tissue irritation.

It will be appreciated by those versed in the drug dispensing art that the present invention advances the state-of-the-art by providing (a) a delivery system that can provide in vivo a multiplicity of tiny osmotic drug delivery devices that can deliver drug-in-solution as the devices travel through the biological environment; (b) a delivery system that can provide tiny osmotic devices for minimizing gastrointestinal irritation; (c) a delivery system that can provide tiny osmotic devices for continuous and steady release for producing constant and steady absorption of delivered drug; and (d) provide a delivery system that can deliver drug from a plurality of tiny osmotic device in solution in the stomach and/or the intestine over time. Also it will be understood by those knowledgeable in the delivery art that many embodiments of this invention can be made without departing from the spirit and scope of the invention, and the invention is not to be construed as limiting, as it embraces all equivalents thereof.

We claim:

1. A method for improving the bioavailability and the absorption of a gastrointestinal administrable drug formulation and for minimizing local irritation of the biological drug receiving environment, wherein the method comprises:
    (a) admitting a primary delivery system into the gastrointestinal tract, the primary delivery system comprising:
        (1) a wall that surrounds a lumen, the wall comprising at least in part a pH sensitive composition that releases at least some of the contents of the lumen in response to a pH environment of 1 to 8;
        (2) a multiplicity of secondary dosage forms in the lumen of the primary delivery system, the secondary dosage forms comprising:
            (a) a wall comprising a composition that is impermeable to the passage of drug, which wall surrounds and defines a compartment;
            (b) a beneficial gastrointestinal administrable drug formulation in the compartment;
            (c) means for releasing the drug from the secondary dosage form, said means comprising at least one of (i) a preformed passageway, (ii) a passageway formed by bioerosion, (iii) a passageway formed by leaching, and (iv) a passageway formed by rupture; and,
            (d) administering the beneficial drug by the primary delivery system releasing at least some of its secondary dosage forms which secondary dosage forms delivers the beneficial drug through at least one of passageway (i), (ii), (iii) and (iv) to the gastrointestinal tract to produce the desired effects.

2. A delivery system for delivering a dosage form that administers a beneficial drug formulation to the gastrointestinal tract, the delivery system comprising:
    (a) a wall that surrounds a lumen, the wall comprising at least in part a pH sensitive composition means for releasing at least some of the contents of the lumen in response to the gastrointestinal tract in response to its pH environment of 1 to 8;
    (b) a multiplicity of dosage forms in the lumen of the delivery system, the dosage forms comprising:
        (1) a wall comprising a composition impermeable to the passage of drug which wall defines a compartment;
        (2) a beneficial gastrointestinal administrable drug formulation in the compartment;
        (3) means for releasing the drug from the dosage form, said means comprising at least of (i) a preformed passageway, (ii) a passageway formed by erosion, (iii) a passageway formed by leaching, and (iv) a passageway formed by rupture in the wall of the dosage form, and wherein when the delivery system is in a gastrointestinal tract;
    (c) the delivery system releases at least some of the dosage forms, which dosage forms administer the beneficial drug through at least one of passageway (i), (ii), (iii) and (iv) to the gastrointestinal tract for improving the bioavailability and the absorption of the gastrointestinal administrable drug, and for minimizing local irritation of the biological drug receiving gastrointestinal environment.

* * * * *